United States Patent
Owen et al.

(10) Patent No.: US 10,495,570 B2
(45) Date of Patent: Dec. 3, 2019

(54) MEASUREMENT OF HYDROCARBON FUEL GAS COMPOSITION AND PROPERTIES FROM TUNABLE DIODE LASER ABSORPTION SPECTROMETRY

(71) Applicant: ABB Schweiz AG, Zurich (CH)

(72) Inventors: Kyle Owen, East Palo Alto, CA (US); Manish X. Gupta, Mountain View, CA (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 15/283,965

(22) Filed: Oct. 3, 2016

(65) Prior Publication Data

US 2018/0095031 A1 Apr. 5, 2018

(51) Int. Cl.
*G01N 21/39* (2006.01)
*G01N 21/359* (2014.01)
(Continued)

(52) U.S. Cl.
CPC ............... *G01N 21/39* (2013.01); *G01J 3/42* (2013.01); *G01N 21/3504* (2013.01);
(Continued)

(58) Field of Classification Search
None
See application file for complete search history.

(56) References Cited

U.S. PATENT DOCUMENTS 5,822,058 A * 10/1998 Adler-Golden ...... G01N 21/359
356/300
6,795,190 B1 9/2004 Paul et al.
(Continued)

FOREIGN PATENT DOCUMENTS

WO 2008144372 A1 11/2008

OTHER PUBLICATIONS

Paper: "Voigt profile", https://en.wikipedia.org/wiki/Voigt_profile, 5 pages.
(Continued)

*Primary Examiner* — Edwin C Gunberg
(74) *Attorney, Agent, or Firm* — Barnes & Thornburg LLP (57) ABSTRACT

A tunable diode laser absorption spectrometer and a method of processing absorption spectra is used to measure concentrations of selected fuel gas components and calculate several fuel gas parameters, including heating value, relative density, compressibility, theoretical hydrocarbon liquid content and Wobbe index. In the described incarnation, a tunable laser diode directs near-infrared light into an optical cavity through a sample of fuel gas. A sensor measures intensity of light exiting the cavity as the laser wavelength is tuned over a specified range to construct a cavity-enhanced absorption spectrum for the fuel gas. A set of basis spectra for expected component species is used to analyze the spectrum and determine component concentrations, including methane, ethane, carbon dioxide, and other discrete and structured absorbers. Critically, a generic broadband absorption is used to model higher hydrocarbons that present themselves as nearly featureless absorption spectra. The fuel gas parameters are then calculated directly from determined component concentrations and the broadband absorption representing the higher hydrocarbons.

26 Claims, 8 Drawing Sheets

(51) Int. Cl.
  *G01N 21/3504* (2014.01)
  *G01N 33/22* (2006.01)
  *G01J 3/42* (2006.01)

(52) U.S. Cl.
  CPC ......... *G01N 21/359* (2013.01); *G01N 33/225* (2013.01); *G01N 2021/399* (2013.01)

(56) References Cited

U.S. PATENT DOCUMENTS

| | | | |
|---|---|---|---|
| 9,255,841 B2* | 2/2016 | Witinski | G01J 3/42 |
| 2006/0092423 A1* | 5/2006 | Servaites | G01N 21/359 |
| | | | 356/437 |

OTHER PUBLICATIONS

Paper: "Using novel laser absorption based analyzers for trace hydrogen sulfide (H2S) measurement", ABB/Los Gatos Research, Article AT/Analytica1/008-EN, 4 pages.

D.S. Baer et al., "Sensitive absorption measurements in the near-infrared region using off-axis integrated-cavity-output spectroscopy", Applied Physics B/Laser and Optics, Rec'd May 6, 2002-Revised May 31, 2002, published Sep. 2, 2002, 6 pages.

M. Bradley, "Curve fitting in raman and IR spectroscopy: Basic theory of line shapes and applications", Thermo scientific—Application note: 50733, 2007, 4 pages.

F. Dong et al., Rapid, online quantification of H2S in JP-8 fuel reformate using near-infrared cavity-enhanced laser absorption spectroscopy, ACS Publications, American Chemical Society, 2011, 83, pp. 4132-4136.

M. Gupta et al., Quantitative determination of the Q(1) quadrupole hydrogen absorption in the near infrared via off-axis ICOS, Chemical Physics Letter 418, 2006, pp. 11-14.

L. Le et al., Development of a rapid on-line acetylene sensor for industrial hydrogenation reactor optimization using off-axis integrated cavity output spectroscopy, Applied Spectroscopy, vol. 62, No. 1, 2008, pp. 59-65.

J. Tennyson et al., Recommended isolated-line profile for representing high-resolution spectroscopic transitions (IUPAC Technical Report), Pure Appl. Chem., 2014, 86(12), pp. 1931-1943.

European Patent Office, International Search Report for PCT/IB2017/001204, dated Jan. 4, 2018, 6 pages.

European Patent Office, Written Opinion of the International Searching Authority for PCT/IB2017/001204, dated Jan. 4, 2018, 7 pages.

Y. Mitsumoto et al., "Laser Spectroscopic Multi-component Hydrocarbon Analyzer", Yokogawa Technical Report English Edition, vol. 56, No. 2, Jan. 1, 2013, 4 pages.

Gas Processors Association, "Calculation of Gross Heating Value, Relative Density, Compressibility and Theoretical Hydrocarbon Liquid Content for Natural Gas Mixtures for Custody Transfer", API Manual of Petroleum Measurement Standards Chapter 14.5, Jan. 1, 2009, 48 pages.

Loubar et al., "A combustionless determination method for combustion properties of natural gases", Fuel, IPC Science and Technology Press, Guildford, GB, vol. 86, No. 16, Oct. 9, 2007, pp. 2535-2544.

N. Makhoukhi et al., "Determination of the composition of a mixture of gases by infrared analysis and chemometric methods", Journal of Molecular Structure., vol. 744-747, Jun. 1, 2005, pp. 855-859.

* cited by examiner

| Item # | HHV Heating Val (Btu/sft3) | Mix 1 M7111-P-108 | Mix 1 Heating Value | Mix 2 M7113-P-108 | Mix 2 Heating Value | Mix 3 MND00225-P-108 | Mix 3 Heating Value |
|---|---|---|---|---|---|---|---|
| Nitrogen | 0 | 4.990% | 0 | 9.000% | 0 | 2.520% | 0 |
| Methane | 1010 | 70.386% | 711 | 64.050% | 647 | 90.509% | 914 |
| Carbon Dioxide | 0 | 1.010% | 0 | 0.500% | 0 | 1.010% | 0 |
| Ethane | 1770 | 9.000% | 159 | 12.500% | 221 | 4.020% | 71 |
| Propane | 2516 | 6.040% | 152 | 7.000% | 176 | 1.020% | 26 |
| Isobutane | 3252 | 3.000% | 98 | 2.970% | 97 | 0.306% | 10 |
| N-Butane | 3262 | 3.040% | 99 | 2.980% | 97 | 0.306% | 10 |
| Isopentane | 4001 | 1.020% | 41 | 0.510% | 20 | 0.051% | 2 |
| N-Pentane | 4009 | 1.010% | 40 | 0.490% | 20 | 0.050% | 2 |
| Helium | 0 | 0.504% | 0 | 0.000% | 0 | 0.000% | 0 |
| n-hexane | 4756 | 0.000% | 0 | 0.000% | 0 | 0.102% | 5 |
| n-heptane | 5503 | 0.000% | 0 | 0.000% | 0 | 0.102% | 6 |
| n-octane | 6249 | 0.000% | 0 | 0.000% | 0 | 0.000% | 0 |
| n-nonane | 6997 | 0.000% | 0 | 0.000% | 0 | 0.002% | 0 |
| n-decane | 7743 | 0.000% | 0 | 0.000% | 0 | 0.002% | 0 |
| TOTAL | | | 1300 | | 1278 | | 1045 |
| % HC other than CH4 and C2H6 | | 14.614% | | 13.950% | | 1.941% | |
| Measured | | | | | | | |
| Methane (%) | 1010 | 72.0662 | 727.86862 | 65.4101 | 660.64201 | 91.2966 | 922.09566 |
| Ethane (%) | 1770 | 8.995 | 159.2115 | 12.3429 | 218.46933 | 3.76515 | 66.643155 |
| Constant (a.u.) | 6500 | 6.44074 | 418.6481 | 6.00596 | 390.3874 | 0.92038 | 59.8247 |
| CALCULATED | | | 1305.72822 | | 1269.49874 | | 1048.563515 |
| Difference (%) | | | -0.425885153 | | 0.674231341 | | -0.3026004402 |

Fig. 3A

| Mix 5 | | Methane | |
|---|---|---|---|
| MBA00042-P-108 | Heating Value | MBA00042-P-108 | Heating Value |
| 0.763% | 0 | 0.000% | 0 |
| 92.364% | 933 | 100.000% | 1010 |
| 1.520% | 0 | 0.000% | 0 |
| 3.050% | 54 | 0.000% | 0 |
| 1.530% | 38 | 0.000% | 0 |
| 0.255% | 8 | 0.000% | 0 |
| 0.255% | 8 | 0.000% | 0 |
| 0.102% | 4 | 0.000% | 0 |
| 0.101% | 4 | 0.000% | 0 |
| 0.010% | 0 | 0.000% | 0 |
| 0.050% | 2 | 0.000% | 0 |
| 0.000% | 0 | 0.000% | 0 |
| 0.000% | 0 | 0.000% | 0 |
| 0.000% | 0 | 0.000% | 0 |
| | 1052 | | 1010 |
| 2.303% | | 0.000% | |
| 93.2817 | 942.14517 | 100.315 | 1013.1815 |
| 2.913 | 51.5601 | -0.0592385 | -1.048521145 |
| 0.946129 | 61.498385 | 0.005510883 | 0.33207395 |
| | 1055.203655 | | 1012.465053 |
| | -0.259259837 | | -0.244064604 |

*Fig. 3B*

| *Fig. 3A* | *Fig. 3B* |
|---|---|

|  | Specific Gravity | Wobbe Index | Mix 1 M7111-P-108 | Mix 1 Wobbe Index | Mix 2 M7113-P-108 | Mix 2 Wobbe Index |
|---|---|---|---|---|---|---|
| Item # |  |  |  |  |  |  |
| Nitrogen | 0.967 | 0.00 | 4.990% | 0 | 9.000% | 0 |
| Methane | 0.5537 | 1357.33 | 70.386% | 955 | 64.050% | 869 |
| Carbon Dioxide | 1.5189 | 0.00 | 1.010% | 0 | 0.500% | 0 |
| Ethane | 1.0378 | 1737.47 | 9.000% | 156 | 12.500% | 217 |
| Propane | 1.5219 | 2039.47 | 6.040% | 123 | 7.000% | 143 |
| Isobutane | 2.0061 | 2296.01 | 3.000% | 69 | 2.970% | 68 |
| N-Butane | 2.0061 | 2303.07 | 3.040% | 70 | 2.980% | 69 |
| Isopentane | 2.487 | 2537.06 | 1.020% | 26 | 0.510% | 13 |
| N-Pentane | 2.487 | 2542.13 | 1.010% | 26 | 0.490% | 12 |
| Helium | 0.138 | 0.00 | 0.504% | 0 | 0.000% | 0 |
| n-hexane | 2.973 | 2758.32 | 0.000% | 0 | 0.000% | 0 |
| n-heptane | 3.459 | 2958.86 | 0.000% | 0 | 0.000% | 0 |
| n-octane | 3.944 | 3146.60 | 0.000% | 0 | 0.000% | 0 |
| n-nonane | 4.428 | 3325.13 | 0.000% | 0 | 0.000% | 0 |
| n-decane | 4.915 | 3492.59 | 0.000% | 0 | 0.000% | 0 |
| TOTAL |  |  |  | 1425 |  | 1392 |
| % HC other than CH4 and C2H6 |  |  | 14.614% |  | 13.950% |  |
| Measured |  |  |  |  |  |  |
| Methane (%) |  |  | 72.0662 | 978.1731433 | 65.4101 | 887.8281791 |
| Ethane (%) |  |  | 8.995 | 156.2851093 | 12.3429 | 214.4537494 |
| Constant (a.u.) |  |  | 6.44074 | 299.49441 | 6.00596 | 279.27714 |
| CALCULATED |  |  |  | 1433.952663 |  | 1381.559068 |
| Difference |  |  |  | -9 |  | 10 |
| Difference (%) |  |  |  | -0.60 |  | 0.72 |

*Fig. 5A*

|  | Mix 3 |  | Mix 5 |  | Methane |  |
|---|---|---|---|---|---|---|
| MND00225-P-108 | Wobbe Index | MBA00042-P-108 | Wobbe Index | MBA00042-P-108 | Wobbe Index |
| 2.520% | 0 | 0.763% | 0 | 0.000% | 0 |
| 90.509% | 1229 | 92.364% | 1254 | 100.000% | 1357.325824 |
| 1.010% | 0 | 1.520% | 0 | 0.000% | 0 |
| 4.020% | 70 | 3.050% | 53 | 0.000% | 0 |
| 1.020% | 21 | 1.530% | 31 | 0.000% | 0 |
| 0.306% | 7 | 0.255% | 6 | 0.000% | 0 |
| 0.306% | 7 | 0.255% | 6 | 0.000% | 0 |
| 0.051% | 1 | 0.102% | 3 | 0.000% | 0 |
| 0.050% | 1 | 0.101% | 3 | 0.000% | 0 |
| 0.000% | 0 | 0.010% | 0 | 0.000% | 0 |
| 0.102% | 3 | 0.050% | 1 | 0.000% | 0 |
| 0.102% | 3 | 0.000% | 0 | 0.000% | 0 |
| 0.000% | 0 | 0.000% | 0 | 0.000% | 0 |
| 0.002% | 0 | 0.000% | 0 | 0.000% | 0 |
| 0.002% | 0 | 0.000% | 0 | 0.000% | 0 |
|  | 1342 |  | 1356 |  | 1357.325824 |
| 1.941% |  | 2.303% |  | 0.000% |  |
|  |  |  |  |  |  |
| 91.2966 | 1239.192329 | 93.2817 | 1266.136604 | 100.315 | 1361.601401 |
| 3.76515 | 65.41821894 | 2.913 | 50.61239838 | -0.0592385 | -1.029249077 |
| 0.92038 | 42.79767 | 0.946129 | 43.99949985 | 0.00510883 | 0.237560595 |
|  | 1347.408218 |  | 1360.744 |  | 1360.809712 |
|  | -6 |  | -5 |  | -3 |
|  | -0.43 |  | -0.34 |  | -0.26 |

MEASUREMENT OF HYDROCARBON FUEL GAS COMPOSITION AND PROPERTIES FROM TUNABLE DIODE LASER ABSORPTION SPECTROMETRY

TECHNICAL FIELD

The present invention relates to measuring chemical constituents and associated properties of hydrocarbon fuel mixtures, and further relates to tunable diode laser absorption spectrometry gas analyzers.

BACKGROUND ART

Whenever fuel gas (natural gas, coal syngas, biogas, etc.) is generated, transferred or used, its level of contamination, heating value, relative density, compressibility, theoretical hydrocarbon liquid content, and Wobbe index are typically required. Measurement of various contaminants (e.g. $H_2S$, $H_2O$, $O_2$, $CO_2$) is critical for preventing infrastructure damage due to corrosion or chemical reactivity. Natural gas producers must clean extracted natural gas to remove contaminants and then verify any residual levels before it is introduced into a pipeline. Desulfurizer beds in fuel reformers need periodic replacement or regeneration to prevent $H_2S$ breakthrough into the reformed fuel product, and so require frequent contaminant level monitoring. Measurement of key gas parameters, including heating value, relative density, compressibility, theoretical hydrocarbon liquid content, and Wobbe index, are critical for pricing the fuel, optimizing burner conditions, and determining combustion efficiency.

Fuel producers and their customers typically use up to four separate analyzers (e.g. electrochemical, chilled mirror, lead tape, and gas chromatographs) to analyze fuel gas characteristics, such as amounts of trace contaminants or heating value. For example, a customer site might include a lead-tape system to measure $H_2S$, a chilled mirror instrument to measure $H_2O$ and a paramagnetic sensor for $O_2$. Gas chromatographs separate hydrocarbon mixtures into their component species to determine heating value and other gas characteristics (e.g. relative density, compressibility, theoretical hydrocarbon liquid content, and Wobbe index). Each of these analyzers has its own limitations and drawbacks. For example, a lead-tape system requires consumables and frequent servicing, while providing relatively slow readings over a small dynamic range. Likewise, chilled mirror devices are very slow and prone to interference from other condensing components. Finally, gas chromatographs, the current industry standard, are both slow (several minutes per analysis) and require costly consumables and maintenance. The entire suite of instruments is expensive to operate and needs extensive on-site maintenance.

Tunable diode laser absorption spectrometry (TDLAS) has been widely used to measure trace contaminants (e.g. $H_2S$, $H_2O$, $O_2$, $CO_2$ . . . ) in fuel gases and other petrochemicals, but has not been used to determine heating value or other gas characteristics. For example, in a paper by Feng Dong, Christian Junaedi, Subir Roychoudhury, and Manish Gupta, "Rapid, Online Quantification of $H_2S$ in JP-8 Fuel Reformate Using Near-Infrared Cavity-Enhanced Laser Absorption Spectroscopy", Analytical Chemistry 83, pp. 4132-4136 (2011), an off-axis ICOS analyzer operating near 1.59 μm simultaneously quantified $H_2S$, $CO_2$, $CH_4$, $C_2H_4$ and $H_2O$ in reformed military fuel with rapid, highly precise measurements over a wide dynamic range, with low detection limit and minimal cross-interference with other present species. It was suggested that by including additional near-IR diode lasers at other wavelengths, the instrument could be extended to measure other species, including CO and $H_2$.

SUMMARY DISCLOSURE

A tunable diode laser absorption spectrometer utilizing off-axis integrated cavity output spectroscopy (off-axis ICOS) is provided that is capable of measuring fuel gas composition and properties, including heating value, relative density, compressibility, theoretical hydrocarbon liquid content, and Wobbe index, while simultaneously also providing rapid, highly accurate and precise measures of various trace contaminants over a large dynamic range, thus allowing fuel gas producers and customers to replace their current array of analyzers with a single low-cost instrument.

In this incarnation, fuel gas is continuously drawn through the analyzer's optical cavity. The ICOS analyzer, which for example may be equipped with two lasers operating near 1.27 μm and 1.58 μm, measures a cavity-enhanced absorption spectrum and then analyzes it with a multivariate fitting routine, wherein the measured spectrum is fit to a selected chemometric model. Heating value, relative density, compressibility, theoretical hydrocarbon liquid content, and Wobbe index are directly calculated from fitted pre-factors for methane, ethane, other constituents (e.g. $CO_2$, CO, $O_2$ . . . ) and broadband, featureless absorption (which encompasses all higher hydrocarbons) to yield values that are accurate to better than 1%, the targeted range for many users.

The large dynamic range (exceeding 10000) of the off-axis ICOS instrument is especially valuable for calculating heating value, since levels of hydrocarbon constituents in fuel gas can vary widely. Compared to industry standard measurements with gas chromatography which can take several minutes per single measurement, the off-axis ICOS instrument can make a comparable or even more accurate measurement in seconds. Moreover, since ICOS is a first-principles technique it requires little or no calibration, so there is very little downtime.

DETAILED DESCRIPTION

Figure 1:
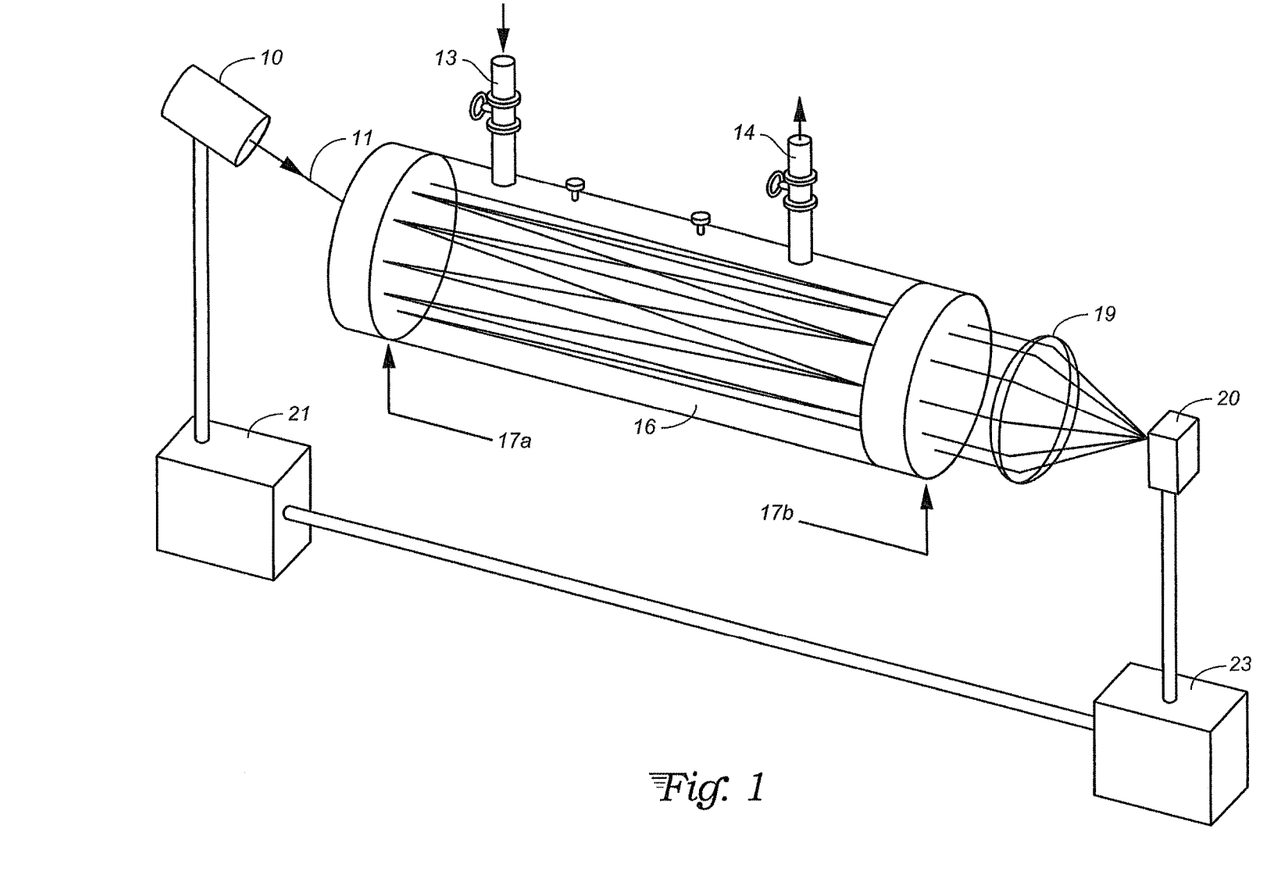
FIG. 1 is a schematic perspective view of an off-axis ICOS instrument in accord with the present invention.

With reference to FIG. 1, in an off-axis ICOS instrument like that described in U.S. Pat. No. 6,795,190, laser light 11 from a tunable near-infrared diode laser 10 is coupled off-axis into a high-finesse optical cavity 16 with two highly reflective (R~99.995%) mirrors 17a and 17b, while fuel gas to be analyzed is flowed through the cavity 16 between gas inlet 13 and gas outlet 14. A near-infrared sensor 20 measures the intensity of light exiting the cavity via a lens 19 as the laser wavelength is tuned over a specified range by means of laser control electronics 21, thereby providing a transmission spectrum that measures wavelength-dependent optical absorption by all of the various chemical components present in the fuel gas. The preferred embodiment utilizes Off-Axis ICOS; however, other tunable diode laser absorption spectrometry methods may also be used.

Choice of wavelength range depends upon the chemical species to be detected, avoiding where possible interfering absorptions from different species. Multiple laser diodes may be available for providing absorption measurements over several different ranges. A preferred embodiment may use two lasers operating near 1.58 μm and 1.27 μm, but other choices are possible. The spectral range over which each laser diode may be tuned is at least 20 GHz and preferably 60-80 GHz. Sensor data is collected and analyzed by a computer system 23, which in accord with the present invention employs chemometric fitting routines and calculations of heating value, relative density, compressibility, theoretical hydrocarbon liquid content, Wobbe index, and contaminant concentrations for the fuel gas stream.

To facilitate line fitting of the measured spectrum, the stored basis sets for use with the chemometric modeling should include individual spectra from each of the expected components in the fuel gas for the wavelength ranges being scanned by the instrument. Thus, an absorption spectrum of pure methane (the dominant constituent of natural gas, coal syngas and biogas) is included. The $CH_4$ spectrum is typically highly structured. Likewise, the basis set also includes the absorption spectrum of ethane ($C_2H_6$). Because the expected percentage of ethane in the fuel gas mixture is lower, it is convenient that the basis spectrum employed be that of a mixture of 10% ethane in inert nitrogen background. This spectrum still retains some structure. The absorption spectra of target contaminants (e.g. $H_2S$, $H_2O$, $O_2$, and $CO_2$) measured in an inert background (e.g. nitrogen or zero-air) are also included. These spectra are typically highly structured. The system is not limited to any particular set of fuel gas components and contaminants and can be extended to other gases with or without fuel values ($H_2$, OCS, etc.) provided a basis spectrum is available for use in the fitting operation. All of these absorption spectra may be empirically determined by filling the cavity with certified concentrations of the components diluted in dry air, nitrogen or other inert gas, and taking the spectra under similar conditions (temperature, pressure, etc.) as the fuel gas measurements to be made. A final basis set "spectrum" included with the chemometric model is a broadband offset basis that is totally featureless (e.g. 10% absorption at all measured wavelengths). This accounts for essentially featureless absorptions by all higher hydrocarbons over the selected wavelength ranges.

Figure 2:
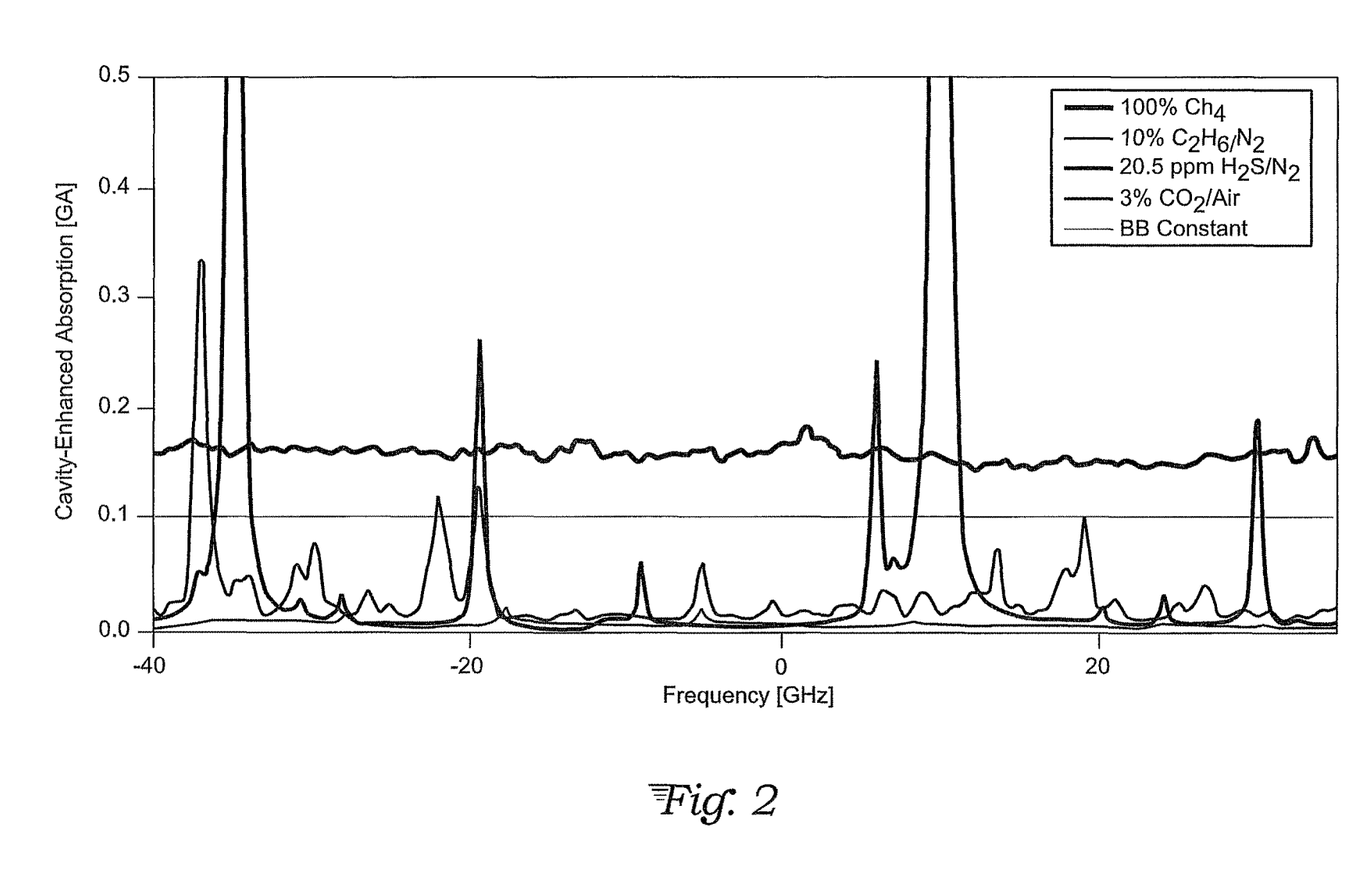
FIG. 2 is a graph of cavity-enhanced absorption versus optical frequency for representative basis sets for analysis of $H_2S$ and $CO_2$ in natural gas. Critically, the basis set includes methane, ethane, and broadband constant that represents higher hydrocarbons and other relatively featureless absorptions.

FIG. 2 shows a representative basis set for chemometric fitting and analysis of natural gas with possible contaminants $H_2S$ and $CO_2$ for the vicinity (−40 GHz to +30 GHz) of 1.58 μm. Here the cavity-enhanced absorption (the y-axis) equals the cavity gain factor G (=R/(1−R), where R is the mirror reflectivity) multiplied by the single-pass absorption A.

A chemometric data analysis strategy like that described in Linh D. Le et al., "Development of a Rapid On-Line Acetylene Sensor for Industrial Hydrogenation Reactor Optimization Using Off-Axis Integrated Cavity Output Spectroscopy", Applied Spectroscopy 62(1), pp. 59-62 (2008) is one known way to quantify the respective constituents. In this scheme, the measured spectrum of a fuel gas is expressed as the sum of the absorption contributions from each individual component in the mixture:

$$A(\nu) = \Sigma_n c_n \cdot A_n(\nu)$$

where $c_n$ is the coefficient that corresponds in a known way to the concentration of the $n^{th}$ component species. This dependence is typically linear and can be determined directly from the basis sets. For example, if a 10% ethane/$N_2$ basis set is used for $A_{ethane}(\nu)$ and $c_a$ for that basis set is 0.1, the calculated concentration of ethane in the fuel gas is 1%. Note that, since the gain factor G is a constant, the coefficients $c_n$ will be the same if cavity-enhanced absorption GA is used instead of the single-pass absorption A.

Once the concentrations $C_a$ of each component species a have been determined, the heating value F is calculated. Heating value F (higher heating value or HHV) for the overall fuel gas mixture is a weighted sum of heating values $F_a$ of the separate component species that add heating value, where concentration of each species constitutes the weight:

$$F = \Sigma_a C_a \cdot F_a$$

Normally, only hydrocarbons found at concentrations exceeding 0.1% contribute to heating value in any meaningful way. Typically, some 10 to 20 species of hydrocarbon with up to 9 carbon atoms contribute. Tabulated heating values may be used, such as 1010 Btu/sft$^3$ (37.6 MJ/m$^3$) for methane and 1770 Btu/sft$^3$ (65.9 MJ/m$^3$) for ethane. These example values depend upon gas density (a function of temperature) and may change depending on the measurement conditions. Heating values per mole or per kilogram are generally constant. All higher hydrocarbons (those other than methane and ethane) are represented here by a measured concentration $C_{BB}$ of an essentially featureless broadband absorber in the spectrum. This contribution can be included by scaling it by an empirical factor E. The heating value F therefore reduces to:

$$F = C_{CH_4} \cdot F_{CH_4} + C_{C_2H_6} \cdot F_{C_2H_6} + C_{BB} \cdot E$$

Note that the equation can be altered in two ways. Additional terms could be added if they have sufficient concentration and heating value (e.g. for hydrogen, acetylene or ethylene) and the ICOS instrument is configured to measure their concentrations (by appropriate selection of diode laser wavelength and inclusion of their spectra in the chemometric basis set). Second, the empirical scaling factor E depends upon the particular broadband basis set employed for the fit and the expected components in the fuel gas mixture. For natural gas and a 10% broadband absorption used for the basis set, a value E=6500 Btu/sft$^3$ (242 MJ/m$^3$) is suitable for accounting for any hydrocarbons other than methane and ethane in the gas. For a substantially different fuel gas mixture (e.g. hydrogen), the empirical factor E will have a different value. Nevertheless, it has been found that this simple method of dealing with the vast array of higher hydrocarbons works across a wide range of natural gas mixtures.

Relative density, compressibility, theoretical hydrocarbon liquid content, and Wobbe index can be calculated in exactly the same way, except that the empirical scaling factor E for the broadband concentration $C_{BB}$ is different. For example, for the Wobbe index:

$$W_w = \Sigma_a C_a \cdot I_{wa} = C_{CH_4} \cdot I_{wCH_4} + C_{C_2H_6} \cdot I_{wC_2H_6} + C_{BB} \cdot E$$

where $I_{wa}$ are the Wobbe index values for each component. These are related to the heating values, but with specific gravity $G_{Sa}$ of each component a separately factored in ($I_{wa}=F_d/\sqrt{G_{Sa}}$). Wobbe index is a measure of the heating value of the quantity of gas that will pass through a hole of a given size in a given amount of time. Since the flow of gas is regulated by an orifice in almost all gas appliances, the Wobbe index can be used to compare actual heating value of different gas blends. The relationship between gas composition and gas parameter for the aforementioned parameters is described in detail in the Gas Processors Associate Standard 2172-09 entitled "Calculation of Gross Heating Value, Relative Density, Compressibility, and Theoretical Hydrocarbon Liquid Content for Natural Gas Mixtures for Custody Transfer."

Figure 3:
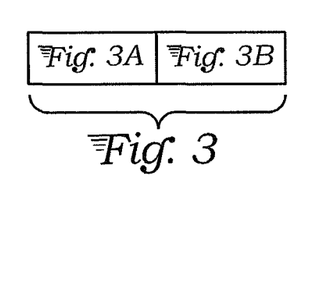
FIG. 3 shows a table, split as indicated by the legend into FIGS. 3A and 3B, of heating value calculations for four distinct blends of fuel gas and pure methane.
Figure 3B:
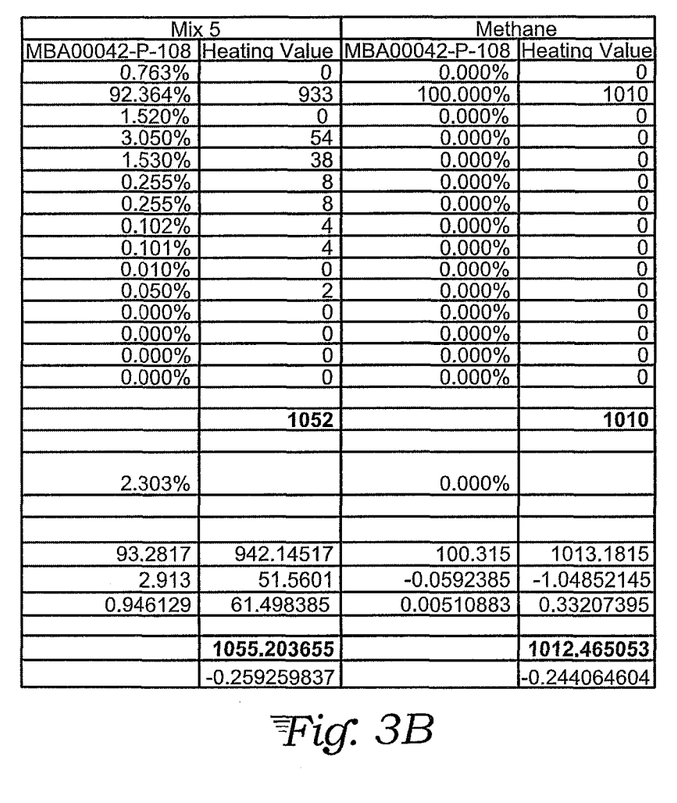
Figure 4:
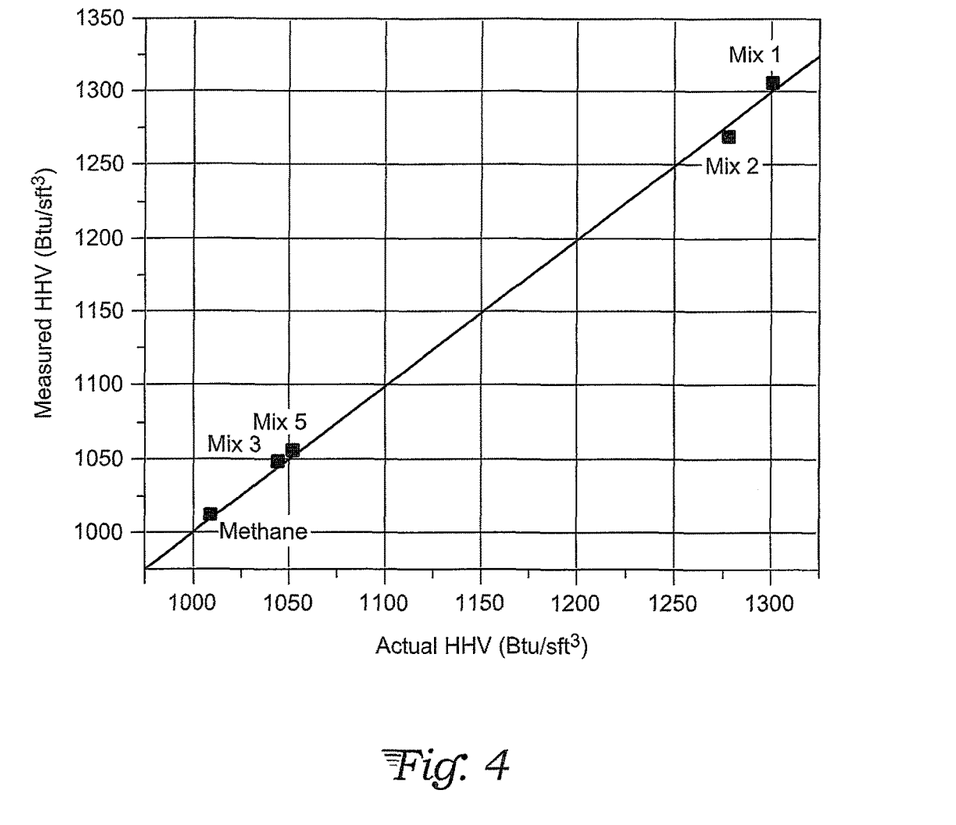
FIG. 4 is a graph of ICOS-measured higher heating values (HHV) versus actual higher heating value for a five fuel gases tabulated in FIG. 3.

FIG. 3 shows a table of heating value calculations for five distinct blends of fuel gas ranging from pure methane (similar to biogas), to a mixture containing high levels of ethane, propane, butanes and pentanes, to still other mixtures even containing hexanes, heptanes, octanes, nonanes and decanes. The respective heating values (high heating value in Btu/sft$^3$) are given on the left, next to each component. The composition of each mixture and the heating value contributions from each component present are given for each of the five fuel gases, together with a sum total. At the bottom of the table are the corresponding ICOS measured concentrations for methane, ethane and broadband absorption and corresponding calculations of the fuel values. As plotted in FIG. 4, it is seen that there is excellent agreement between the actual and measured heating values over a wide dynamic range. Mixture 2 shows the widest deviation, but in all cases, the measurement is accurate to better than ±10 Btu/sft$^3$ and ±1% of actual heating value, which is adequate for many customer applications.

Figure 5:
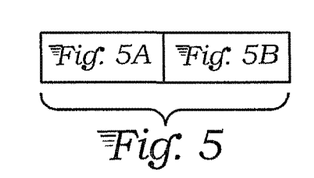
FIG. 5 shows a table, split as indicated by the legend into FIGS. 5A and 5B, of Wobbe index calculations for the same five fuel mixtures as in FIG. 3.
Figure 5A:
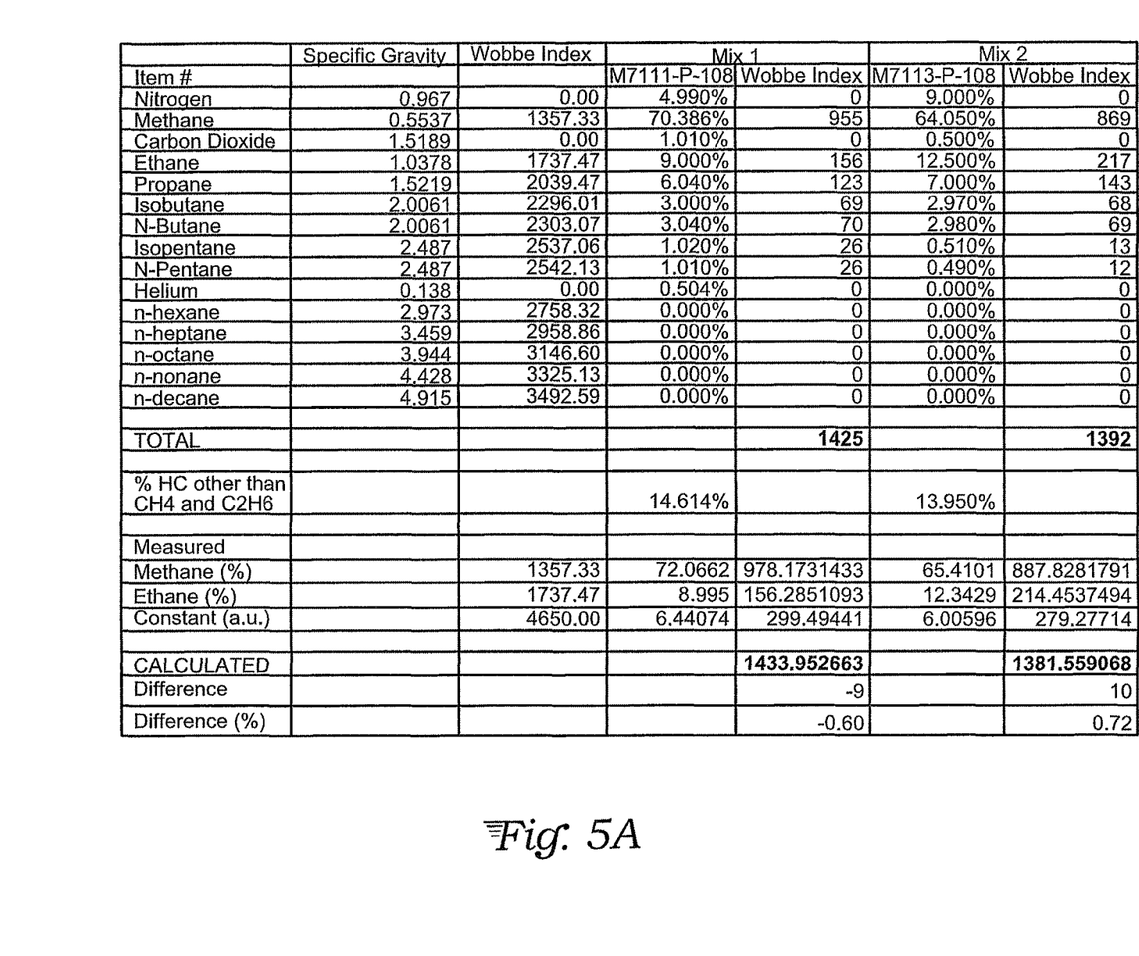
Figure 5B:
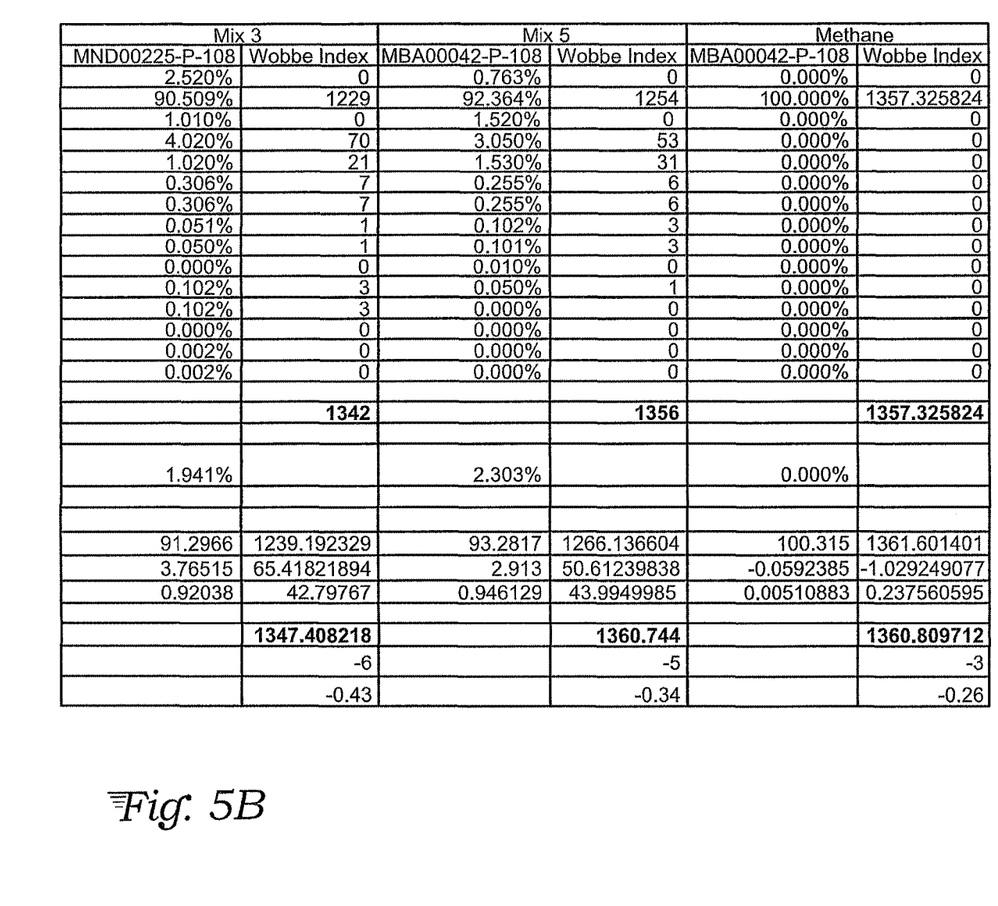
Figure 6:
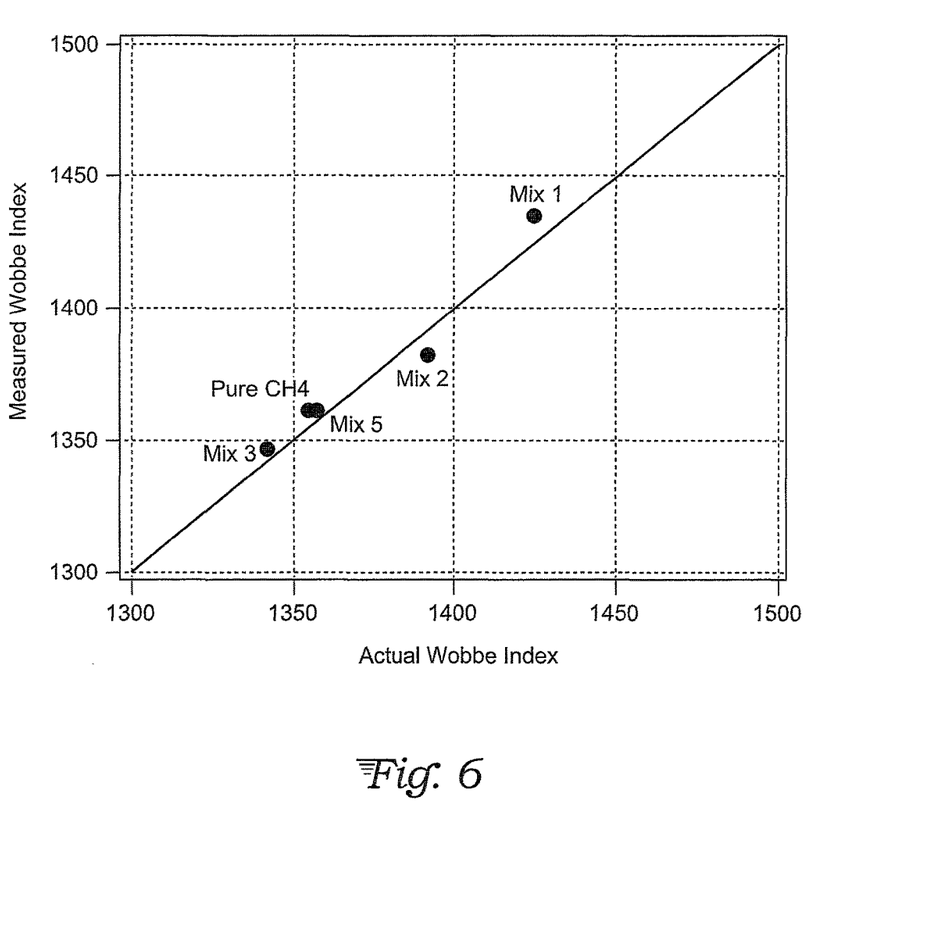
FIG. 6 is a graph of ICOS-measured Wobbe index versus actual Wobbe index for the five fuel gas mixtures tabulated in FIG. 5.

FIGS. 5 and 6 show a similar table and graph of Wobbe index calculations for the same five blends. Again, the ICOS measured Wobbe index is accurate to better than ±1% of actual value. Extending the basis sets to spectra from higher hydrocarbons (three to ten carbon atoms), with appropriate choice of one or more additional laser diode wavelength ranges, should further improve the fit and resulting heating value and Wobbe index calculations to even higher precision. Likewise, optimizing or calibrating the prefactor for the broadband absorption will also improve the results.

Similarly, the relative density G may be calculated by the processor on the basis of determined concentrations for methane ($C_{CH_4}$) and ethane ($C_{C_2H_6}$) and a determined concentration $C_{BB}$ of an offset basis spectrum representing higher hydrocarbons, such that:

$$G=C_{CH_4}\cdot G_{CH_4}+C_{C_2H_6}\cdot G_{C_2H_6}+C_{BB}\cdot E,$$

where $G_{CH_4}$ and $G_{C_2H_6}$ are respective relative densities for methane and ethane, and E is an empirical factor for a composite relative density of all expected higher hydrocarbons in the fuel gas mixture. And likewise, the compressibility Z is calculated by the processor on the basis of determined concentrations for methane ($C_{CH_4}$) and ethane ($C_{C_2H_6}$) and a determined concentration $C_{BB}$ of an offset basis spectrum representing higher hydrocarbons, such that:

$$Z=C_{CH_4}\cdot Z_{CH_4}+C_{C_2H_6}\cdot Z_{C_2H_6}+C_{BB}\cdot E,$$

where $Z_{CH_4}$ and $Z_{C_2H_6}$ are respective compressibility factors for methane and ethane, and E is an empirical factor for a composite compressibility of all expected higher hydrocarbons in the fuel gas mixture. And finally, the theoretical hydrocarbon liquid content L is calculated by the processor on the basis of determined concentrations for methane ($C_{CH_4}$) and ethane ($C_{C_2H_6}$) and a determined concentration $C_{BB}$ of an offset basis spectrum representing higher hydrocarbons, such that:

$$L=C_{CH_4}\cdot L_{CH_4}+C_{C_2H_6}\cdot L_{C_2H_6}+C_{BB}\cdot E,$$

where $L_{CH_4}$ and $L_{C_2H_6}$ are respective theoretical liquid content values for methane and ethane, and E is an empirical factor for a composite theoretical liquid content of all expected higher hydrocarbons in the fuel gas mixture. In each case, the empirical factor will vary according to the fuel gas property being calculated.

Thus, the invention has several advantages over the legacy technologies in use today. TDLAS sensors, and off-axis ICOS analyzers in particular, offer substantially more accurate and precise contamination measurements than lead-tape, chilled mirror and electrochemical sensors. The legacy technologies frequently require recurring calibration to account for changes in detector response, drift and other issues. Since TDLAS (including off-axis ICOS) is a first-principles technique, it requires little or no calibration, but at most only annual reverification. A key advantage in the present invention is speed. Gas chromatography, chilled mirror, lead tape and electrochemical sensors typically take 5 to 10 minutes to make a single measurement. In contrast, TDLAS sensors can make a comparable (or even more accurate) measurement in just 10-20 seconds. This allows customers to actively control their processes in essentially real time to prevent end-product contamination and react quickly to changes in heating value, Wobbe index, and the other properties. Due to high spectral resolution of the laser in TDLAS systems, the analyzers are capable of measuring fuel gas components with little to no cross-interference. Thus, in contrast to electrochemical sensors which have strong chemical interferences (e.g. between $H_2S$ and CO), the present invention's readings are both selective and accurate. Additionally, many of the legacy instruments only operate over a small dynamic range before they saturate. The off-axis ICOS instrument used in the present invention operates over a dynamic range in excess of 10000, allowing customers to detect both trace levels as well as upset conditions. The large dynamic range is especially valuable in calculating heating value, relative density, compressibility, theoretical hydrocarbon liquid content, and Wobbe index; since the concentrations of hydrocarbon constituents can vary widely. Unlike gas chromatographs and lead-tape analyzers, the present system does not require any consumables, resulting in lower operating costs. Indeed, it combines the measurements from multiple legacy instruments into one single instrument capable of measuring heating value, relative density, compressibility, theoretical hydrocarbon liquid content, and Wobbe index calculation, as well as trace contaminant detection and quantification.

What is claimed is:
1. A tunable diode laser absorption spectrometry system for fuel gas measurement, comprising:
   an off-axis integrated cavity output spectroscopy (ICOS) instrument comprising a first tunable laser diode with a first tunable wavelength range providing laser light coupled off-axis into a high-finesse optical cavity, a second tunable laser diode with a second tunable wavelength range providing laser light coupled off-axis into the cavity, a gas inlet and a gas outlet arranged to flow a fuel gas through the cavity, and an optical sensor arranged to measure intensity of laser light exiting the optical cavity, wherein the laser diodes are tuned over their respective wavelength ranges so that the sensor measurement provides a wavelength-dependent optical absorption spectrum; and a computer processor to receive the sensor measurement from the optical sensor, access a database of basis spectra for fuel gas components, process the absorption spectrum with a chemometric fitting routine to determine concentrations of selected fuel gas components, and calculate at least a heating value (F) and an additional value (X) selected from relative density, compressibility, theoretical hydrocarbon liquid content, and Wobbe index from the determined fuel gas component concentrations on the basis of determined concentrations for methane ($C_{CH_4}$) and ethane ($C_{C_2H_6}$) and the determined concentration ($C_{BB}$) of an offset basis spectrum representing higher hydrocarbons such that:

$$X = C_{CH_4} \cdot X_{CH_4} + C_{C_2H_6} \cdot X_{C_2H_6} + C_{BB} \cdot E,$$

where $X_{CH_4}$ and $X_{C_2H_6}$ are respective coefficients for methane and ethane, and E is an empirical factor for a composite relative density, compressibility, theoretical hydrocarbon liquid content, or Wobbe index of all expected higher hydrocarbons in the fuel gas mixture.

2. The system as in claim 1, wherein the database includes basis spectra for at least methane, ethane, together with a broadband offset basis to represent the higher hydrocarbons.

3. The system as in claim 2, wherein the heating value (F) is calculated by the processor on the basis of the determined concentrations for methane and ethane and the determined concentration of the offset basis spectrum representing the higher hydrocarbons, such that:

$$F = C_{CH_4} \cdot F_{CH_4} + C_{C_2H_6} \cdot F_{C_2H_6} + C_{BB} \cdot E,$$

where $F_{CH_4}$ and $F_{C_2H_6}$ are respective heating values for methane and ethane, and E is an empirical factor for a composite heating value of all the expected higher hydrocarbons in the fuel gas mixture.

4. The system as in claim 1, wherein the Wobbe index ($I_w$) is calculated by the processor on the basis of the determined concentrations for methane and ethane and the determined concentration of the offset basis spectrum representing the higher hydrocarbons, such that:

$$I_w = C_{CH_4} \cdot I_{wCH_4} + C_{C_2H_6} \cdot I_{wC_2H_6} + C_{BB} \cdot E,$$

where $I_{wCH_4}$ and $I_{wC_2H_6}$ are respective Wobbe indices for methane and ethane, and E is an empirical factor for a composite Wobbe index of all the expected higher hydrocarbons in the fuel gas mixture.

5. The system as in claim 1, wherein the relative density (G) is calculated by the processor on the basis of the determined concentrations for methane and ethane and the determined concentration of the offset basis spectrum representing the higher hydrocarbons, such that:

$$G = C_{CH_4} \cdot G_{CH_4} + C_{C_2H_6} \cdot G_{C_2H_6} + C_{BB} \cdot E,$$

where $G_{CH_4}$ and $G_{C_2H_6}$ are respective relative densities for methane and ethane, and E is an empirical factor for a composite relative density of all the expected higher hydrocarbons in the fuel gas mixture.

6. The system as in claim 1, wherein the compressibility (Z) is calculated by the processor on the basis of the determined concentrations for methane and ethane and the determined concentration of the offset basis spectrum representing the higher hydrocarbons, such that:

$$X = C_{CH_4} \cdot Z_{CH_4} + C_{C_2H_6} \cdot Z_{C_2H_6} + C_{BB} \cdot E,$$

where $Z_{CH_4}$ and $Z_{C_2H_6}$ are respective compressibility factors for methane and ethane, and E is an empirical factor for a composite compressibility of all expected higher hydrocarbons in the fuel gas mixture.

7. The system as in claim 1, wherein the theoretical hydrocarbon liquid content (L) is calculated by the processor on the basis of the determined concentrations for methane and the ethane and the determined concentration ($C_{BB}$) of the offset basis spectrum representing the higher hydrocarbons, such that:

$$L = C_{CH_4} \cdot L_{CH_4} + C_{C_2H_6} \cdot L_{C_2H_6} + C_{BB} \cdot E,$$

where $L_{CH_4}$ and $L_{C_2H_6}$ are respective theoretical liquid content values for methane and ethane, and E is an empirical factor for a composite theoretical liquid content of all the expected higher hydrocarbons in the fuel gas mixture.

8. The system as in claim 1, wherein concentrations of the selected fuel gas components to be determined include specified fuel gas contaminant species.

9. The system as in claim 8, wherein specified fuel gas contaminant species are selected from any one or more of $H_2S$, $H_2O$, $O_2$, $CO_2$, or OCS.

10. The system as in claim 1, wherein the first wavelength range is a near-infrared wavelength range encompassing absorption bands of the selected fuel gas components with minimal cross-interference.

11. The system as in claim 10, wherein the first wavelength range is in a vicinity of 1.58 µm.

12. The system as in claim 11, wherein the second wavelength range is in a vicinity of 1.27 µm.

13. A method of measuring a heating value for a fuel gas, comprising:

coupling laser light from first and second tunable laser diodes off-axis into a high-finesse optical cavity of an off-axis integrated cavity output spectroscopy (ICOS) instrument, wherein the first and second laser diodes have respective tunable wavelength ranges, flowing a fuel gas from a gas inlet through the cavity to a gas outlet, measuring intensity of laser light exiting the optical cavity using an optical sensor while the laser diodes are tuned over their respective wavelength ranges so that the sensor measurement provides a wavelength-dependent optical absorption spectrum, receiving, with a computer processor, the sensor measurement from the optical sensor, accessing, with the computer processor, a database of basis spectra for fuel gas components, employing, with the computer processor, a chemometric fitting routine to process the absorption spectrum so as to determine concentrations of selected fuel gas components, and calculating, with the computer processor, a heating value (F) and an additional value (X) selected from relative density, compressibility, theoretical hydrocarbon liquid content, and Wobbe index from the determined fuel gas component concentrations on the basis of determined concentrations for methane ($C_{CH_4}$) and ethane ($C_{C_2H_6}$) and the determined concentration ($C_{BB}$) of an offset basis spectrum representing higher hydrocarbons such that:

$$X = C_{CH_4} \cdot X_{CH_4} + C_{C_2H_6} \cdot X_{C_2H_6} + C_{BB} \cdot E,$$

where $X_{CH_4}$ and $X_{C_2H_6}$ are respective coefficients for methane and ethane, and E is an empirical factor for a composite relative density, compressibility, theoretical hydrocarbon liquid content, or Wobbe index of all expected higher hydrocarbons in the fuel gas mixture.

14. The method as in claim 13, wherein the database includes basis spectra for at least methane, ethane, together with a broadband offset basis to represent the higher hydrocarbons.

15. The method as in claim 14, wherein the heating value (F) is calculated by the processor on the basis of the determined concentrations for methane and ethane and the determined concentration of the offset basis spectrum representing the higher hydrocarbons, such that:

$$F = C_{CH_4} \cdot F_{CH_4} + C_{C_2H_6} \cdot F_{C_2H_6} + C_{BB} \cdot E,$$

where $F_{CH_4}$ and $F_{C_2H_6}$ are respective heating values for methane and ethane, and E is an empirical factor for a composite heating value of all the expected higher hydrocarbons in the fuel gas mixture.

16. The method as in claim 13, wherein the Wobbe index ($I_w$) is calculated by the processor on the basis of the determined concentrations for methane and ethane and the determined concentration of the offset basis spectrum representing the higher hydrocarbons, such that:

$$I_w = C_{CH_4} \cdot I_{wCH_4} + C_{C_2H_6} \cdot I_{wC_2H_6} + C_{BB} \cdot E,$$

where $I_{wCH_4}$ and $I_{wC_2H_6}$ are respective Wobbe indices for methane and ethane, and E is an empirical factor for a composite Wobbe index of all the expected higher hydrocarbons in the fuel gas mixture.

17. The method as in claim 13, wherein the relative density (G) is calculated by the processor on the basis of the determined concentrations for the methane and ethane and the determined concentration of the offset basis spectrum representing the higher hydrocarbons, such that:

$$G = C_{CH_4} \cdot G_{CH_4} + C_{C_2H_6} \cdot G_{C_2H_6} + C_{BB} \cdot E,$$

where $G_{CH_4}$ and $G_{C_2H_6}$ are respective relative densities for the methane and ethane, and E is an empirical factor for a composite relative density of all the expected higher hydrocarbons in the fuel gas mixture.

18. The method as in claim 13, wherein the compressibility (Z) is calculated by the processor on the basis of the determined concentrations for methane and ethane and the determined concentration of the offset basis spectrum representing the higher hydrocarbons, such that:

$$Z = C_{CH_4} \cdot Z_{CH_4} + C_{C_2H_6} \cdot Z_{C_2H_6} + C_{BB} \cdot E,$$

where $Z_{CH_4}$ and $Z_{C_2H_6}$ are respective compressibility factors for the methane and ethane, and E is an empirical factor for a composite compressibility of all the expected higher hydrocarbons in the fuel gas mixture.

19. The method as in claim 13, wherein the theoretical hydrocarbon liquid content (L) is calculated by the processor on the basis of the determined concentrations for the methane and ethane and the determined concentration of the offset basis spectrum representing the higher hydrocarbons, such that:

$$L = C_{CH_4} \cdot L_{CH_4} + C_{C_2H_6} \cdot L_{C_2H_6} + C_{BB} \cdot E,$$

where $L_{CH_4}$ and $L_{C_2H_6}$ are respective theoretical liquid content values for methane and ethane, and E is an empirical factor for a composite theoretical liquid content of all the expected higher hydrocarbons in the fuel gas mixture.

20. The method as in claim 13, wherein concentrations of the selected fuel gas components determined by the processor include specified fuel gas contaminant species.

21. The method as in claim 20, wherein specified fuel gas contaminant species are selected from any one or more of $H_2S$, $H_2O$, $O_2$, $CO_2$, or OCS.

22. The method as in claim 13, wherein the wavelength range of the first diode is a near-infrared wavelength range encompassing absorption bands of the selected fuel gas components with minimal cross-interference.

23. The method as in claim 22, wherein the wavelength range of the first diode is in a vicinity of 1.58 μm.

24. The method as in claim 23, wherein the wavelength range of the second laser diode is in a vicinity of 1.27 μm and is coupled into the optical cavity to obtain an absorption spectrum in a second wavelength range.

25. The system as in claim 1, wherein the first laser diode is tunable over a spectral range of at least 20 GHz, and wherein the second laser diode is tunable over a spectral range of 60-80 Ghz.

26. The method as in claim 13, wherein the first laser diode is tunable over a spectral range of at least 20 GHz, and wherein the second laser diode is tunable over a spectral range of 60-80 Ghz.

* * * * *